(12) United States Patent
Dallago

(10) Patent No.: US 11,185,711 B2
(45) Date of Patent: Nov. 30, 2021

(54) DEVICE FOR THE TREATMENT OF THE HUMAN BODY USING ELECTROMAGNETIC FIELDS

(71) Applicant: S.I.S.T.E.M.I. S.R.L.—SOCIETA' ITALIANA SEQEX TECNOLOGIE ELETTRO MEDICALI INNOVATIVE, Pergine Valsugana (IT)

(72) Inventor: Valerio Dallago, Piazze di Bedollo (IT)

(73) Assignee: S.I.S.T.E.M.I. S.R.L.—SOCIETA' ITALIANA SEQEX TECNOLOGIE ELETTIRO MEDICALI INNOVATIVE, Pergine Valsugana (IT)

( * ) Notice: Subject to any disclaimer, the term of this patent is extended or adjusted under 35 U.S.C. 154(b) by 294 days.

(21) Appl. No.: 16/099,944

(22) PCT Filed: May 11, 2017

(86) PCT No.: PCT/EP2017/061374
§ 371 (c)(1),
(2) Date: Nov. 8, 2018

(87) PCT Pub. No.: WO2017/194693
PCT Pub. Date: Nov. 16, 2017

(65) Prior Publication Data
US 2019/0134416 A1 May 9, 2019

(30) Foreign Application Priority Data
May 13, 2016 (IT) .......................... 102016000049169

(51) Int. Cl.
*A61N 2/02* (2006.01)
*A61M 21/00* (2006.01)
(Continued)

(52) U.S. Cl.
CPC ................ *A61N 2/02* (2013.01); *A61B 5/024* (2013.01); *A61B 5/0205* (2013.01); *A61B 5/053* (2013.01);
(Continued)

(58) Field of Classification Search
CPC .......... A61N 2/004; A61N 2/002; A61N 2/02; A61B 5/0205; A61B 5/0476;
(Continued)

(56) References Cited

U.S. PATENT DOCUMENTS

2010/0004551 A1  1/2010  Lingg

FOREIGN PATENT DOCUMENTS

DE  3244582 A1  12/1984
EP  0422253 A1  4/1991
(Continued)

OTHER PUBLICATIONS

International Search Report dated Jun. 22, 2017 re: Application No. PCT/EP2017/061374, pp. 1-4, citing: WO 2010/025114 A1, EP 1 100 583 A1, US 2010/0004551 A1, WO 2014/145284 A2 and WO 2004/082759 A2.
(Continued)

*Primary Examiner* — Christine H Matthews
*Assistant Examiner* — Joshua Daryl D Lannu
(74) *Attorney, Agent, or Firm* — Cantor Colburn LLP

(57) ABSTRACT

A device for treatments on the human body with variable magnetic fields, which is provided with:
at least one electric waveform generator to be connected to at least one Helmholtz coil to be brought close to the person or persons to be treated and producing variable low-intensity and low-frequency magnetic fields. The device further includes
at least one impedance meters with electrode terminals to be applied to the person in order to assess the effectiveness of the waves of the generator; and
(Continued)

at least one electronic processing unit for the management of the waveform generator or generators as a function of the measurements of the impedance meter and of memory parameters stored in the processing unit.

11 Claims, 1 Drawing Sheet

(51) Int. Cl.

| | | |
|---|---|---|
| *A61N 2/00* | (2006.01) | |
| *A61B 5/0205* | (2006.01) | |
| *A61B 5/00* | (2006.01) | |
| *G16H 20/30* | (2018.01) | |
| *A61B 5/024* | (2006.01) | |
| *A61B 5/053* | (2021.01) | |
| *A61B 5/08* | (2006.01) | |
| *A61B 5/318* | (2021.01) | |
| *A61B 5/369* | (2021.01) | |
| *A61B 5/377* | (2021.01) | |

(52) U.S. Cl.
CPC ............ *A61B 5/0816* (2013.01); *A61B 5/318* (2021.01); *A61B 5/369* (2021.01); *A61B 5/377* (2021.01); *A61B 5/4836* (2013.01); *A61M 21/00* (2013.01); *A61N 2/002* (2013.01); *A61N 2/004* (2013.01); *G16H 20/30* (2018.01); *A61M 2021/0027* (2013.01)

(58) Field of Classification Search
CPC ..... A61B 5/4836; A61B 5/024; A61B 5/0402; A61B 5/053; A61B 5/0816; A61B 5/0484; A61M 21/00; A61M 2021/0027; G16H 20/30
See application file for complete search history.

(56) References Cited

FOREIGN PATENT DOCUMENTS

| WO | 0007664 A1 | 2/2000 | |
|---|---|---|---|
| WO | WO-0007664 A1 * | 2/2000 | .............. A61N 2/02 |
| WO | 2004082759 A2 | 9/2004 | |
| WO | 2010025114 A1 | 3/2010 | |
| WO | WO-2010025114 A1 * | 3/2010 | ........... G06F 19/325 |
| WO | 2014145284 A2 | 9/2014 | |

OTHER PUBLICATIONS

IT Search Report dated Nov. 30, 2016 re: Application No. IT UA20163405, pp. 1-8, citing: WO 2010/025114 A1, EP 1 100 583 A1, US 2010/0004551 A1, WO 2014/145284 A2 and WO 2004/082759 A2.

Written Opinion dated Jun. 22, 2017 re: Application No. PCT/EP2017/061374, pp. 1-6, citing: WO 2010/025114 A1, EP 1 100 583 A1, US 2010/0004551 A1, WO 2014/145284 A2 and WO 2004/082759 A2.

* cited by examiner

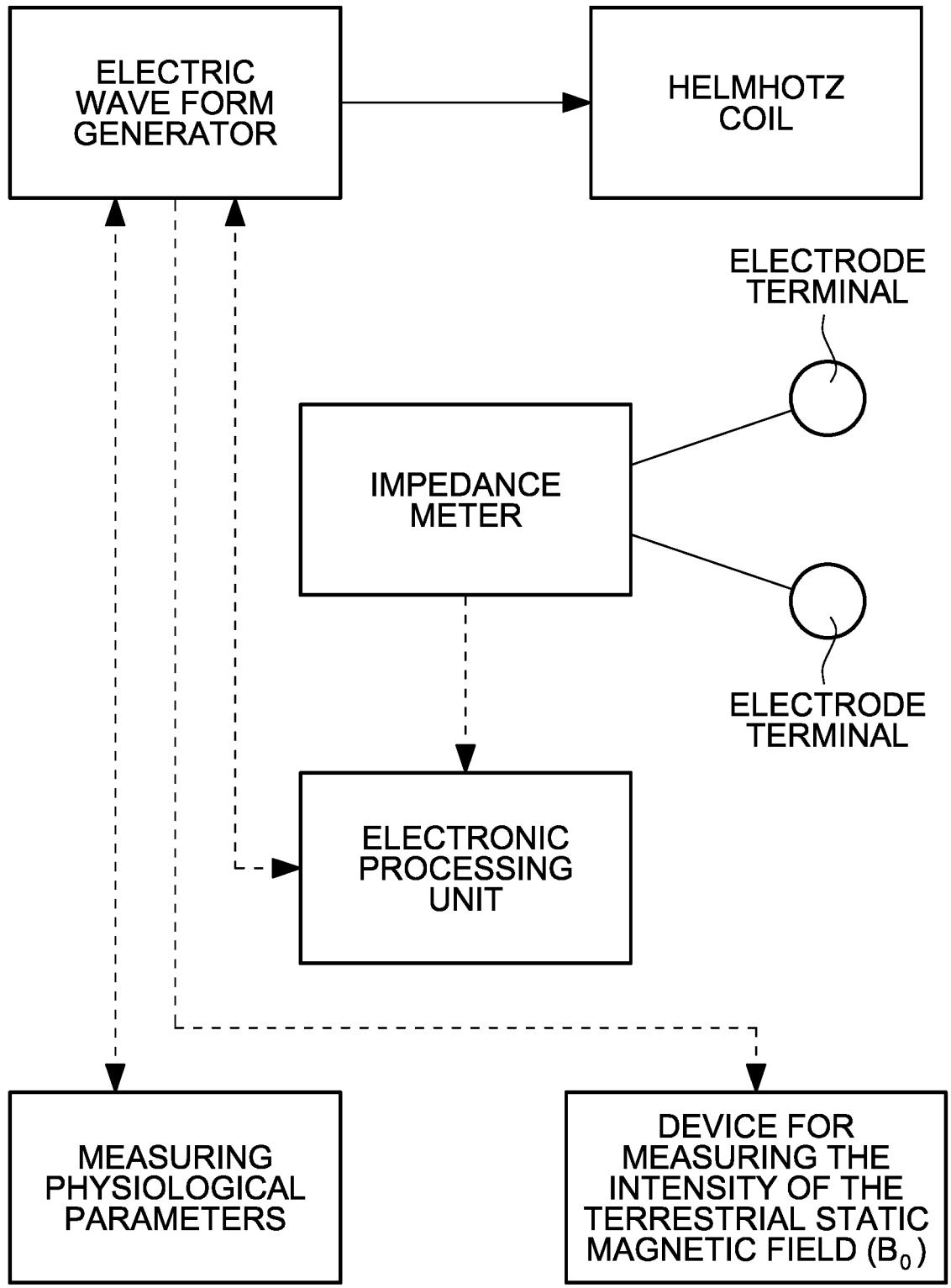

DEVICE FOR THE TREATMENT OF THE HUMAN BODY USING ELECTROMAGNETIC FIELDS

TECHNICAL FIELD

The present disclosure relates to a device for the treatment of the human body, and in general for the improvement of oxidative balance, by way of using electromagnetic fields.

BACKGROUND

On the market there are several different types of apparatus that use electromagnetic fields, such as, for example, magnetotherapy devices, which use field intensities, frequencies and waveforms that are gleaned from empirical practice, or other apparatuses that take advantage of the phenomenon known as ICR-like, or Ion Cyclotron Resonance-like, in order to increase ion mobility in biological systems.

The theory that describes the use of such Ion Cyclotron Resonance-like for the therapeutic use was first formulated by American biophysicist Abraham R. Liboff in 1985, and it is currently the best scientific explanation for the interaction of ultraweak electromagnetic fields with biological systems.

Currently apparatuses are widespread for treatments on the human body with magnetic fields, which irradiate the human body proper by way of E.L.F. magnetic fields (i.e. fields characterized by low intensity, up to a few Gauss, and low frequency, in the order of tens of Hertz).

Such apparatuses start from the assumption that such standard magnetic fields can bring some benefit without taking account of the peculiarities of the individual patients.

Devices of this type are for example described in DE3244582 and in EP422253.

Also known, from EP1100583 in the name of S.I.S.T.E.M.I. Srl, is an apparatus for treatments on the human body with variable magnetic fields, which comprises:
- at least one electric waveform generator to be connected, by way of a cable, to Helmholtz coils to be brought close to the person to be treated and producing variable low-intensity and low-frequency magnetic fields;
- at least one impedance meter, with electrode terminals to be applied to the person in order to assess the effectiveness of the waves of the generator;
- at least one electronic processing unit for the management of the waveform generator or generators as a function of the measurements of the impedance meter and of memory parameters stored in the processing unit.

The solution described in EP1100583, although offering considerable advantages over the other apparatuses currently on the market, exhibits some limitations in terms of optimization of the process of identifying the optimal characteristic waves for the patient and in terms of delivering them.

In this regard, it should be noted that one of the greatest problems to take into consideration is that the effectiveness of the treatment, which as mentioned avails of using electromagnetic fields, is influenced enormously by the intensity of the terrestrial static magnetic field.

SUMMARY

The aim of the present disclosure is to make available a device for the treatment of the human body that is capable of overcoming the above mentioned drawbacks.

Within this aim, the disclosure ensures a treatment on the human body that is repeatable and independent of the variability of the terrestrial magnetic field and which, therefore, is "adaptive" with respect to the variability of the terrestrial magnetic field.

The disclosure devises a device for the treatment of the human body that can make it possible to take account, for the choice of the type of waves to generate, not only of the impedance of the patient but also of additional parameters.

The present disclosure provides a device for the treatment of the human body that is capable of improving, with use, the compliance between the treatment delivered and the therapeutic requirements, by virtue of a process of ongoing learning.

Finally, with the present disclosure it is intended to overcome the technical difficulties that obstruct obtaining an irradiated field of uniform intensity and therefore of known characteristics that can easily be reproduced.

This aim and these and other advantages which will become better apparent hereinafter are achieved by providing a device for the treatment of the human body according to the following claims.

Further characteristics and advantages of the disclosure will become better apparent from the description of some preferred, but not exclusive, embodiments of a device for treating the human body.

BRIEF DESCRIPTION OF THE DRAWINGS

FIG. 1 illustrates a device, according to the disclosure, for treatments on a human body with variable magnetic fields.

DETAILED DESCRIPTION OF THE DISCLOSURE

In the exemplary embodiments illustrated below, individual characteristics shown in relation to specific examples may in reality be interchanged with other, different characteristics, existing in other exemplary embodiments.

The present disclosure relates to a device for treatments on the human body with variable magnetic fields, which is provided with:
- at least one electric waveform generator to be connected to at least one Helmholtz coil to be brought close to the person or persons to be treated and producing variable low-intensity and low-frequency magnetic fields;
- at least one impedance meter, with electrode terminals to be applied to the person in order to assess the effectiveness of the waves of the generator;
- at least one electronic processing unit for the management of the waveform generator or generators as a function of the measurements of the impedance meter and of memory parameters stored in the processing unit.

As will be better explained hereinbelow, the device comprises, furthermore:
- at least one device for measuring the heart rate and/or respiratory rate of the detected signal both by way of electrodes or other means to be applied to the person, and by way of a ballistic system (for example with an accelerometer) to be applied to the bed on which the person lies, in order to assess the effectiveness of the waves of the generator, and acquire information on the state of health and its variation over time including by way of statistical analysis; and/or
- at least one EEG meter with electrode terminals or other means to be applied to the cranium of the person in order to evaluate the impact of the waves on the brain rhythms and/or on the person's state of health.

Conveniently, the electronic processing unit is adapted to manage the waveform generator or generators also as a function of the other measurement systems, which comprise the heart rate and/or respiratory rate meter and/or the EEG meter.

It has been proven experimentally that certain biologically important ionic species, when given a certain value of terrestrial static magnetic field (the value of which hereinafter will be referred to as $B_0$), increase their mobility when subjected to a resonance frequency the value of which depends on the mass m of that ion, on its charge $Z_i$ and on the value $B_0$, according to the following relationship:

$$\text{Frequency} = B_0(Z_i/2\pi * m)$$

The electric waveform generator has a first mode of use in association with the impedance meter and/or other parameters for the optimization of the waveforms with which the body of a specific patient is to be treated, and a second mode of use in which the aforementioned electric waveform generator delivers to the specific patient the waveform or waveforms identified by the management electronic processing unit in operation: measurements of the impedance meter during the first mode of use and/or measurements of other parameters originating from the HRV (i.e. heart rate variation) measuring device and/or of the breathing rhythm and/or of the variation of brain rhythms and of memory parameters stored in the processing unit.

By way of example, it is possible for the waveform generator to comprise a first waveform generation apparatus to be used in the first mode of use (and optionally in the second mode of use), which is integrated or can be integrated with the impedance meter and/or with the other measurement devices and associated with the management electronic processing unit, and a second waveform generation apparatus associated with a data processor corresponding to the waveforms identified by the management electronic processing unit.

Delving deeper into the details, the device has a data processing unit, typically a microprocessor, which is functionally connected to an applicator that is adapted to generate an electromagnetic field.

The device comprises a unit for inputting environmental and operational data and data about the patient being treated.

In output, the data processing unit can be advantageously connected to a data storage medium, which has been found to be particularly useful if treatments need to be performed automatically, with the specifications of the treatment contained on the storage medium, and therefore doing away with a specialist operator.

Conveniently, such data storage medium can be constituted by a smart card and/or by a contactless device using NFC/RFID technology.

According to a further aspect of the present disclosure, the waveform generator, in the first mode of use, is associated with a device for measuring the intensity of the terrestrial static magnetic field (indicated with B0) along the axis of the field generated by the applicator, and with a device for storing the intensity of the terrestrial static magnetic field measured during such first mode of use.

The waveform generator is associated, in the second mode of use also, with a device for measuring the intensity of the terrestrial static magnetic field.

The data item related to the intensity of the terrestrial magnetic field measured in the second mode of use (i.e. during the treatment of the body) is sent to the data processing unit, which acts on the waveforms identified by the management electronic processing unit on the basis of a database for correlation of ion mobility as a function of the intensity of the terrestrial magnetic field.

In more detail, operation entails the operator being able to choose one or more electrolytes and entering their symbol into the program (for example K+ for potassium or Ca++ for calcium). Based on the (static) geomagnetic environmental field the device will automatically calculate the value of the ion resonance frequency for each ionic species chosen. Simultaneously, in the first mode of use the device will measure the impedance measurement response in order to identify the optimal waveform for each subject to be treated in relation to the ionic species selected, so that the treatment is personalized not only for the ionic species but also for the impedance measurement response.

According to a particularly important aspect of the present disclosure, as previously mentioned, the device, in the first mode of use, is associated, in addition to the impedance meter with electrode terminals to be applied to the person, with an additional device for measuring physiological parameters of the patient, which is chosen from the group comprising:

a device for measuring the heart rate of the patient;
a device for measuring the electrical activity of the heart of the patient (electrocardiogram, ballistocardiography measurement etc.);
a device for measuring the respiratory functionality of the patient (such as for example a spirometer);
a device for measuring the electrical activity of the brain (electroencephalogram);
and combinations thereof.

Specifically, the optimization of the waveform or waveforms to be delivered in the second mode of use, i.e. during the treatment, will be done using not only the data item acquired by the impedance meter but also the variation, following the application of the various types of waves, of such further physiological parameters.

For the purposes of example, the optimization of the waveform or waveforms to be delivered can occur if, following the delivery by the generator of specific waveforms, a normalization is found of the physiological parameters measured by the additional measuring devices.

Likewise, the waveform generator can be associated, in the second mode of use also, with devices for measuring physiological parameters so as to monitor the effectiveness of the treatment over time.

Furthermore, the variation of the physiological parameters over time, as a function of the type of treatment, can be stored and collected in a database that can be used by the data processing unit in order to optimize the characteristics of the waves in patients who have similar initial situations.

Preferably, the data processing unit is connected in output to a first frequency generator (in this regard it has been found to be particularly advantageous to have such first frequency generator be constituted by a cyclotron frequency generator) and to a generator of an "undulation" frequency that is higher than the frequency generated by the first frequency generator, and therefore generally higher than the cyclotron frequency.

Such undulation frequency can, optionally, also be in a harmonic relationship with the cyclotron frequency.

According to a preferred embodiment, the data processing unit further can be connected in output to a white noise or pink noise (filtered white noise) generator and to a generator of predetermined waveforms that have been found to be particularly effective in experimental practice, when emitted at the desired cyclotron frequency.

The generator of predetermined waveforms with cyclotron frequency or other frequencies, such as for example, those of brain rhythms, the undulation frequency generator and optionally, if present, the noise generator can be connected individually via a respective switch to an adder which in turn is connected, by way of a power interface, to at least one applicator.

Conveniently, the switches make it possible to add the outputs of the blocks at will.

The power interface (constituted for example by a voltage/current converter) is adapted to drive the subsequent applicator or applicators.

According to a further aspect of the present disclosure, it is possible for the data processing unit to manage multiple different waveform generators connected to the respective applicators.

For the purposes of example, one or more applicators can be functionally connected to a generator of predetermined waveforms with cyclotron-like frequency or other frequencies, one or more applicators can be connected to the undulation frequency generator and optionally, if they are present, one or more applicators can be connected to the noise generator.

It is possible for the applicators to be optionally, at least partially, mutually overlapping.

There is no reason why each applicator cannot be optionally associated with an adder according to what is described above.

The applicator is adapted to generate, in the desired region of space, an electromagnetic field with suitable characteristics of intensity and uniformity.

According to a particularly important aspect of the present disclosure, the or each applicator can be constituted by an inductor which is provided so as to be supported by a structure on which the patient can lie or into which he or she can be inserted as in a tunnel, and with such dimensions as to irradiate the human body in an optimal manner.

However, there is no reason why the applicator or applicators cannot be integrated inside the space where the patients live: for the purposes of example, the applicator can be integrated in the floor or in the walls of a dwelling or of a room, in carpets or vertical divider panels, in bathtubs, chairs, armchairs, sofas, beds etc.

Entering the environmental and operational data can be done with an adapted keypad, a video terminal, a PC, a smartphone, a tablet computer, or even remotely by way of specific management software.

The resistance and capacitive reactance values of the body, detected by way of the impedance meter and conveniently processed, can be used by the operator to adjust the parameters of the therapy, or by the data processing unit to set the treatment automatically.

The physiological data, such as for example HRV, heart rate, breathing rate, impedance and other data that will be progressively measured by the device, the treatment parameters chosen by the operator or automatically by the device, the geomagnetic field values and other values can all be used immediately by the device as a guidance system for selecting the parameters of the best therapy and/or sent to a central collection and data processing unit. The processing of such data can be geared to identify and progressively prepare more effective treatment protocols, and also to reprogram the automatic programs of the devices proper, as well as being used to provide statistics and indications to improve protocols and/or renew the technology employed.

The data collected by the device can be sent to the central collection and data processing unit by way of the fixed-line or mobile network, or analyzed by way of a computer and used directly by the operator, or analyzed automatically by the device itself and be stored on a magnetic data storage medium in order to perform the therapy. There is no reason why the data cannot also be transmitted remotely via web to domestic devices connected to the network or other means for the execution of residential treatments.

The central collection and data processing unit will perform collection, statistical analysis and analysis of correlations between different variables such as for example:
  the subjective data of the patient, state of health and progress before, during and after administration of the treatments (anonymously);
  the physiological data, such as for example HRV, heart rate, breathing rate, EEG;
  the values corresponding to his or her impedenziometry;
  the treatment parameters chosen by the operator or automatically by the device;
  the environmental data, such as the geomagnetic field and its variations including over time;
  other data that are acquired as time goes on.

Conveniently, the applicator can be associated with a laser or pulsed-light point delivery device, or with a light diffuser for larger parts or for the entire body.

The impedance meter with electrode terminals to be applied to the person in order to assess the effectiveness of the waves of the generator can measure the overall impedance of the body of the patient but also, for particular disorders limited to some specific parts of the body, the impedance variation of such specific parts of the body of the patient.

All the characteristics of the disclosure, indicated above as advantageous, convenient or similar, may also be missing or be substituted by equivalent characteristics.

The disclosure, thus conceived, is susceptible of numerous modifications and variations, all of which are within the scope of the appended claims.

In practice it has been found that in all the embodiments the disclosure has achieved the intended aims and advantages.

In particular, the device has been found to be particularly effective for improving the quality of life in patients affected by chronic degenerative diseases, for rehabilitation and recovery of the motor and psycho-physical functions in patients struck down by severe events such as for example a stroke or a heart attack, for the reduction of side effects and for improving the quality of life in patients undergoing chemotherapy, radiotherapy and surgery.

In practice the materials employed, as well as the dimensions and the contingent shapes, may be any according to requirements.

Moreover, all the details may be substituted by other, technically equivalent elements.

The disclosures in Italian Patent Application No. 102016000049169 (UA2016A003405) from which this application claims priority are incorporated herein by reference.

The invention claimed is:
1. A device for treatments on a human body with variable magnetic fields, the device comprising:
  at least one electric waveform generator to be connected to at least one Helmholtz coil adapted to be brought close to a patient to be treated and producing variable low-intensity and low-frequency magnetic fields;

at least one impedance meter, with electrode terminals adapted to be applied to the patient in order to assess effectiveness of waveform or waveforms of the at least one electric waveform generator; and at least one management electronic processing unit for management of the at least one waveform generator as a function of measurements of the at least one impedance meter and of memory parameters stored in the at least one management electronic processing unit;

said at least one electric waveform generator having a first mode of use in association with said at least one impedance meter and/or other parameters for optimization of the waveforms with which the human body of a specific patient is to be treated, and a second mode of use in which said at least one electric waveform generator delivers to the specific patient the waveform or waveforms identified by the at least one management electronic processing unit, wherein in the first mode of use, said device is associated with at least one additional device configured for measuring physiological parameters of the patient, which is chosen from the group comprising:

a device configured for measuring heart rate of the patient;

a device configured for measuring electrical activity of the heart of the patient;

a device configured for measuring respiratory functionality of the patient;

a device configured for measuring electrical activity of the brain of the patient; and combinations thereof, wherein in said first mode of use, said at least one electric waveform generator receives information about an intensity of a terrestrial static magnetic field (B0) along an axis of a field generated by an applicator associated with a device configured for storing the information about the intensity of the terrestrial static magnetic field (B0) received during said first mode of use, said at least one electric waveform generator is associated, in the second mode of use also, with the information about the intensity of the terrestrial static magnetic field (B0), and a data item related to the intensity of the terrestrial magnetic field measured in the second mode of use is sent to a data processing unit, which is adapted to act on the waveform or waveforms identified by the at least one management electronic processing unit on a basis of a database for correlation of ion mobility as a function of the intensity of the terrestrial magnetic field.

2. The device according to claim 1, wherein said at least one electric waveform generator is associated, in said second mode of use, with at least one of the devices configured for measuring physiological parameters of the patient, so as to monitor effectiveness of treatment over time.

3. The device according to claim 1, further comprising means of storing and collecting data related to variation of the physiological parameters over time, as a function of type of treatment, in the database that can be used by the data processing unit in order to optimize characteristics of the waveform or waveforms in patients.

4. The device according to claim 1, wherein said data processing unit is connected in output to a first frequency generator and to a generator of an undulation frequency that is higher than a frequency generated by the first frequency generator.

5. The device according to claim 4, wherein said data processing unit can be connected in output to a white noise or pink noise generator and to a generator of predetermined waveforms that have a cyclotron frequency or brain rhythm frequencies.

6. The device according to claim 4, wherein said undulation frequency generator and a noise generator are connected individually by way of a respective switch to an adder, which in turn is connected by way of a power interface to said applicator.

7. The device according to claim 1, wherein said data processing unit manages said at least one electric waveform generator and at least one additional electric waveform generator that are connected to respective applicators.

8. The device according to claim 7, wherein each applicator comprises an inductor that is adapted to be supported by a structure on which the patient can lie or in a tunnel into which the patient can be inserted, and with dimensions configured to irradiate the human body in an optimal manner.

9. The device according to claim 1, wherein data collected by said device can be sent to a central collection and said data processing unit by way of a fixed-line or mobile network, or analyzed by way of a computer and used directly by an operator, or analyzed automatically by the device itself and be stored on a data storage medium in order to perform therapy.

10. The device according to claim 1, wherein said applicator can be associated with a laser or pulsed-light point delivery device, or with a light diffuser for larger parts or for an entire body.

11. The device according to claim 1, wherein said at least one impedance meter with electrode terminals adapted to be applied to the patient in order to assess the effectiveness of waveform or waveforms of the at least one electric waveform generator is adapted to measure an overall impedance of the body of the patient or, for particular disorders limited to some specific parts of the body, also impedance variation of said specific parts of the body of the patient.

* * * * *